United States Patent [19]

Jackisch

[11] Patent Number: 4,686,311

[45] Date of Patent: * Aug. 11, 1987

[54] DEHYDROHALOGENATION OF HALOETHYL BROMINATED BENZENES

[75] Inventor: Philip F. Jackisch, Baton Rouge, La.

[73] Assignee: Ethyl Corporation, Richmond, Va.

[*] Notice: The portion of the term of this patent subsequent to Dec. 27, 2000 has been disclaimed.

[21] Appl. No.: 536,361

[22] Filed: Sep. 27, 1983

Related U.S. Application Data

[63] Continuation-in-part of Ser. No. 130,119, Mar. 13, 1980, Pat. No. 4,423,262.

[51] Int. Cl.$^4$ .............................................. C07C 17/34
[52] U.S. Cl. .................................. 570/193; 570/200; 502/164
[58] Field of Search ............... 570/200, 228, 229, 193; 502/164

[56] References Cited

U.S. PATENT DOCUMENTS

| | | | |
|---|---|---|---|
| 2,290,758 | 7/1942 | Levine et al. | 260/650 R |
| 2,541,022 | 2/1951 | Baxter | 570/229 |
| 2,561,516 | 7/1951 | Ladd et al. | 260/650 R |
| 2,996,554 | 8/1961 | Olah et al. | 260/650 R |
| 3,065,280 | 11/1962 | Vogt | 260/654 D |
| 3,204,004 | 8/1965 | Sexton | 585/436 |
| 3,664,966 | 5/1972 | Gordon | 260/654 D |
| 3,737,469 | 6/1973 | Berger et al. | 570/200 |
| 3,755,476 | 8/1973 | Crary et al. | 570/229 |
| 3,867,468 | 2/1975 | Vofsi et al. | 260/650 R |
| 3,896,181 | 7/1975 | Brown et al. | 260/654 D |
| 3,936,508 | 2/1976 | Wenzel et al. | 570/229 |
| 3,966,831 | 6/1976 | Levy et al. | 570/200 |
| 4,267,388 | 5/1981 | Darkes et al. | 570/193 |
| 4,292,453 | 9/1981 | Daren et al. | 570/193 |
| 4,308,410 | 12/1981 | Hall et al. | 570/229 |
| 4,423,262 | 9/1983 | Jackisch | 570/193 |

OTHER PUBLICATIONS

J. Dockx, Quaternary Ammonium Compounds in Organic Synthesis, pp. 441-456, In Synthesis, 1973.

Fieser et al, Reagents for Organic Synthesis, p. 911, John Wiley & Sons (1967).

*Primary Examiner*—Donald B. Moyer
*Assistant Examiner*—Joseph A. Boska
*Attorney, Agent, or Firm*—Donald L. Johnson; John F. Sieberth; Paul H. Leonard

[57] ABSTRACT

A process for the preparation of bromostyrenes which comprises aqueous alcoholic alkali dehydrohalogenation of a 1-haloethyl bromobenzene, a 2-haloethyl bromobenzene, or a 1-methyl-2-haloethyl brominated benzene in the presence of a phase transfer catalyst at a temperature of between about 0° C. and about 150° C. The bromostyrenes have the particular utility as a comonomer for the preparation of a co-polymer exhibiting a flame retardancy. Both bromostyrenes and brominated alpha-methyl styrenes are formed.

19 Claims, No Drawings

DEHYDROHALOGENATION OF HALOETHYL BROMINATED BENZENES

CROSS-REFERENCE

This application is a continuation-in-part of U.S. patent application Ser. No. 130,119, filed Mar. 13, 1980 now U.S. Pat. No. 4,423,262.

BACKGROUND OF THE INVENTION

This invention relates to the dehydrohalogenation of a 1- or 2-haloethyldibromobenzene. More particularly, this invention relates to the dehydrohalogenation of a haloethylhalobenzene in an aqueous alcoholic alkaline medium using a phase transfer catalyst. This invention also relates to the dehydrohalogenation of 1- and 2-haloethyl monobromobenzene, 1- and 2-haloethyl polybromobenzene, and mixtures thereof.

DESCRIPTION OF THE PRIOR ART

Various methods of preparation of dibromostyrene are known. Most involve dehydrobromination of either 1-bromoethyldibromobenzene or 2-bromoethyldibromobenzene and also the dehydration of the 1-hydroxyethyldibromobenzene.

The various methods of dehydration of 1-hydroxyethyldibromobenzene include the use of $Al_2O_3$ i.e. passing the 1-hydroxyethyldibromobenzene over $Al_2O_3$ at about 280° C. This is reported in *Chem. Abstracts* by M. M. Koton (1953) as having only a 57 percent yield.

British Patent No. 986,634, is an application of dehydrobromination to both the 1-haloethylbromobenzene and 1-haloethylbromobenzene It describes a method of using $CaSO_4$ as a catalyst. The chosen haloethylbromobenzene is passed over granular calcium sulfate with superheated steam at a temperature of 180° to 350° C. Other catalysts mentioned in the literature are CaC12 and CaO.

U.S. Pat. No. 3,737,469 describes the preparation of bromostyrene simultaneously with an alkyl bromide. This process is conducted by beginning with either 2-bromoethylbromobenzene or 2-bromoethylbromobenzene and reacting the selected compound with a molten alkali metal bromide or with an alkaline earth bromide at a temperature between about 250° C. to 500° C. in the presence of an alkanol. The alkanol acts as a scavenger agent picking up liberated HBr, thus favoring the formation of the products.

U.S. Pat. No. 3,867,468 describes a process for the simultaneous production of dibromostyrene and an alkyl bromide by reacting bromoethyldibromobenzene and an alkanol. When beginning with 1-bromoethyldibromobenzene, the reactants are contacted with molten alkali metal bromides or alkaline earth metal bromides at 300°–500° C. When beginning with the 2-bromoethyldibromobenzene, the reaction temperature suggested is 400°–550° C. to effect a pyrolysis reaction. Here again the alkanol is used as a scavenger to accept the eliminated HBr, termed a "reactive-diluent".

U.S. Pat. No. 3,980,722 also describes a method of producing dibromostyrene simultaneously with an alkyl bromide. This process is conducted by reacting bromoethyl-dibromobenzene with an alkanol at an elevated temperature in the gaseous phase at about 400°–550° C. Another improvement described in this patent is the presence of peroxides or other sources of free radicals to act as a catalyst. Thus, conducting the reaction of the catalyst allows a substantially lower temperature to effect the reaction of about 280° C.

U.S Pat. No. 3,966,831 describes a method of production of dibromostyrene by reacting 2-bromoethyl-dibromobenzene in the presence of water or alkanol and a free radical source such as a peroxide at a temperature between 280° C. and 470° C.

The use of quaternary salts of Group V-A elements with the formula $(R_1R_2R_3R_4M)+X$ as phase transfer catalysts are described in U.S. Pat. No. 3,992,432. This patent depicts a method of catalyzing a reaction in which the reactants in a heterogeneous medium are located in two distinct or separate phases of differing polarity.

The use of quaternary ammonium halide salt as a phase transfer catalyst in various elimination reactions is suggested in the literature. W. P. Weber and G. W. Gokel, *Phase Transfer Catalysis in Organic Synthesis*, 1977, (p. 125), depict the use of phase transfer catalyst for dehydrohalogenatin of alkyl halides and of a 1-halo-olefins to yield acetylenes. They suggest a phase transfer catalyst such as tetrabutyl ammonium bromide (or bisulfate) to convert 1,2-dibromoethylbenzene to phenylacetylene.

J. Dockx, in *Quaternary Ammonium Compounds in Organic Synthesis* reports the use of a phase transfer catalyst in the production of styrene from phenethylbromide in 50 percent NaOH.

SUMMARY OF THE PRESENT INVENTION

The present invention provides a process for the production of ar-dibromostyrene via dehydrobromination of a 2-bromoethyldibromobenzene by reacting 2-bromoethyldibromobenzene with a tertiary alcohol in the presence of a phase transfer catalyst in an alkaline medium. The present invention also provides a process for the production of a bromostyrene such as ar-monobromostyrene or any of the ar-substituted polybromostyrenes, or mixtures thereof via dehydrohalogenation of a 1- or 2-haloethyl bromobenzene by reacting same with a tertiary alcohol in the presence of a phase transfer catalyst in an alkaline medium.

DESCRIPTION OF PREFERRED EMBODIMENTS

In the process of the present invention 2-bromoethyldibromobenzene is contacted with an alkali metal hydroxide, an alkali metal halide, a lower alkyl tertiary alcohol and a phase transfer catalyst to produce ar-dibromostyrene. Also, according to the process of the present invention, 2-haloethyl monobromobenzene 2-haloethyl polybromobenzene, and mixtures thereof are contacted with an alkali metal hydroxide, an alkali metal halide, a lower alkyl tertiary alochol, and a phase transfer catalyst to produce bromostyrenes.

The precursor compounds of the invention are the haloethyl bromobenzenes other than 2-bromoethyl dibromobenzene and including both the mono- and polybromobenzenes of this class.

Examples of the 1- and 2- haloethylbromobenzenes of the invention are:

1-chloroethyl monobromobenzene
2-chloroethyl monobromobenzene
1-bromoethyl dibromobenzene
2-chloroethyl tribromobenzene
2-bromoethyl tetrabromobenzene
1-bromoethyl pentabromobenzene
2-chloroethyl dibromobenzene 2-bromoethyl monobromobenzene
1-chloroethyl dibromobenzene
2-bromoethyl tribromobenzene
2-bromoethyl pentabromobenzene.

The invention is also suitable to form various brominated alpha-methylstyrenes as well. Thus the term haloethyl bromobenzene includes the 1-methyl-2-haloethyl bromobenzenes such as:
1-methyl-2-chloroethyl dibromobenzene;
1-methyl-2-bromoethyl dibromobenzene;
1-methyl-2-chloroethyl tribromobenzene;
1-methyl-2-chloroethyl pentabromobenzene;
1-methyl-2-bromoethyl tetrabromobenzene; and the like.

Various other chloroethyl and bromoethyl bromobenzenes are also workable according to the invention. Also, various mixtures of the starting materials are well suited for the invention.

The 2-bromoethyl compounds are preferred.

Examples of bromostyrene dehydrohalogenated products of the invention include:
ar,ar-dibromostyrene
ar,ar,ar-tribromostyrene
ar-monobromostyrene
2,4-dibromostyrene
2,3,4,5,6-pentabromostyrene Also included are the brominated alpha-methylstyrenes such as ar, ar-dibromo alpha-methylstyrene 2,3,5,-tribromo alpha-methylstyrene and the like as well as mixtures thereof.

The alkali metal hydroxide is used in a concentrated solution of about 20 percent or greater. Sodium and potassium hydroxides are preferred. Sodium hydroxide is the most preferred as it is the least expensive. A saturated solution or nearly saturated sodium hydroxide solution, say, 50–60 percent, is the most preferred. Concentrations outside these ranges may be employed, though not with good results.

An alkali metal halide, or other source of common ion, is used to saturate the solution and thus force a movement of other reactants toward dissolution in the organic phase. Sodium chloride and potassium chloride are preferred. Sodium chloride (in conjunction with sodium hydroxide as the alkali metal hydroxide) is most preferred as it is readily available in purified form and is also most economical. A quantity sufficient to saturate the alkali metal hydroxide is preferred.

The lower alkyl tertiary alcohol is the source of a strong alkoxide ion and acts as a promoter and catalyst in the dehydrobromination. A lower alkyl tertiary alcohol of about 4 to about 7 carbon atoms is preferred. 2-Hydroxy-2-methylpropane, i.e., tert-butanol, is most preferred due to base strength and ease of removal by water washing after reaction is completed.

The phase transfer catalyst is used in order to favor optimum extraction of the dehydrobromination or dehydrohalogenation reagents into the organic phase, particularly the t-butoxide ion formed under the process described in this invention. A tetraalkyl quaternary ammonium halide having 8–17 carbon atoms is suitable. Triethylpentyl ammonium bromide is preferred because of its ability to optimize the solubility of t-butoxide in the organic medium, thus yielding an increase in the rate of elimination. Other alkyl quaternary ammonium halides may be employed.

The reaction is carried out at a temperature in the range of about 0° C. to about 150° C. and preferably between about 20° C. and about 45° C.

The t-butyl alcohol and triethylamyl ammonium bromide can be used in substantially stoichiometric quantities or present in concentrations of about 0.05 mole to about 10 moles of t-butyl alcohol and about 0.001 to about 1.0 moles of triethylamyl ammonium bromide per 1 mole of substrate, 2-bromoethyldibromobenzene.

Although NaOH and KOH are preferred, other caustic substances can provide the alkaline medium, and although NaCl and KCl are preferred, any organic or inorganic (salt) compound which will aid in saturation can be employed.

The process of the present invention has the advantage of giving high yields of ar-dibromostyrene as a monomer. It has the added advantage of being conducted at a low temperature while still providing a good yield at a good rate. The ability to be conducted at low temperature also eliminates the need for sudden quenching of the product to prevent polymerization. The above described advantages are also applicable to produce high yields of aromatic monobromostyrene, aromatic polybromostyrene, aromatic mono- and polybromo alpha-methylstyrene, and mixtures thereof as monomer.

This invention also is less costly than methods requiring sodium ethoxide in ethanol or potassium t-butoxide in t-butanol. The ability to proceed at a lower temperature also increases the safety in preparing dibromostyrene, monobromostyrene, higher bromostyrenes, and mixtures thereof.

The following examples are illustrative and not limiting of the process of the present invention.

COMPARATIVE EXAMPLE 1 ar-Dibromostyrene via Phase Transfer Catalyzed Dehydrobromination

A solution of 147.90 g. (0.431 mole) of 2-bromoethyldibromobenzene in 250 ml. of methylene chloride was stirred for 7 ks (2 hours) at 5 Hz (300 rpm) at 313 K. (40° C.) with 150 g (2.25 mole) of 60 percent sodium hydroxide solution and 3.12 g. (0.0124 mole) of triethylpentyl ammonium bromide. The product was washed with three 500-ml portions of water, dried over calcium sulfate (Drierite), and stripped of solvent in a rotary evaporator at a bath temperature of 323 K. (50° C.). The yield of product was 106.97 g. (77.2 per cent of theory). GC analysis showed 27.1 percent of the desired ar-dibromostyrene, the remainder being largely unreacted starting material.

COMPARATIVE EXAMPLE 2

A solution of 168.3 g (0.491 mole) of 2-bromoethyldibromobenzene in 200 ml. of methylene chloride was stirred for 7 ks (2 hours) at 5 Hz (300 rpm) at 298 K. (25° C.( with 200 g (2.5 mole) of 50 percent sodium hydroxide solution and 3.10 g (0.0123 mole) of triethylpentyl ammonium bromide. The product was washed with five 500 ml portions of water, dried over calcium sulfate (Drierite), and stripped of solvent in a rotary evaporator at a bath temperature of 323 K. (50° C.). The yield of product was 119.32 g (81.6 percent of theory). GC analysis showed 55.7 percent of the desired ar-dibromostyrene, the remainder being largely unreacted starting material. The following two examples, 3 and 4, disclose the advantage of the invention by supplying a promoter quantity of t-alkoxide ion.

EXAMPLE 3

A mixture of 337 g (0.983 mole) of 2-bromoethyl-dibromobenzene, 337 g of ar-dibromostyrene contaminated with 2-bromoethyl dibromobenzene, 200 g (2.50 mole) of 50 percent sodium hydroxide solution, 2 g of sodium chloride, 10 ml (7.79 g. 0.105 mole) of t-butanol and 3 g (0.0119 mole) of triethylpentyl ammonium bromide was stirred 3.5 ks (1 hour) at 5 Hz (300 rpm) at 318 K. (45° C.). The phases were separated after 500 ml of water was added and the organic phase was stirred with fresh sodium hydroxide saturated with sodium chloride, fresh t-butanol, and fresh phase transfer catalyst for an additional 3.6 ks. The yield of product was 438 g. GC analysis showed 0.78 percent ar-bromostyrene, 96.43 percent ar-dibromostyrene, and 2.79 percent ar-tribromostyrene with no starting material present.

When 1.4852 g of the product was diluted with 5 ml of acetone and then 5 ml of methanol, solid polymer precipitated. This was washed with fresh solvent, then dried in a vacuum dessicator at 363 K. (90° C.) for 14 ks (4 hours). The weight of polymer was 0.3155 g (21.24 percent of the product mixture).

EXAMPLE 4

A mixture of 174.6 g (0.509 mole) of 2-bromoethyl-dibromobenzene, 200 g (2.50 mole) of 50 percent sodium hydroxide solution, 2 g of sodium chloride, 10 ml (7.79 g. 0.105 mole) of t-butanol, and 6.5 g (0.0258 mole) of triethylpentyl ammonium bromide was stirred for 7 ks (2 hours) at 5 Hz (300 rpm at 313 K. (40° C.). GC analysis showed an 87.8 percent conversion of starting material to ar-dibromostyrene. Stirring was continued for another 7 ks and GC analysis showed the conversion to be 98.2 percent. The product was washed with 500 ml portions of water, dried over calcium sulfate (Drierite), and stirred under a high vacuum (33 Pa or 0.2 torr) for ks (30 minutes). The yield of product was 111.55 g (83.2 percent of theory).

EXAMPLE 5 ar-Dibromostyrene

A solution of sodium ethoxide was prepared by dissolving 52.8 g (2.296 gram-atoms) of sodium metal in 800 ml of absolute ethanol. To this solution was added 624.74 g (1.822 mole) of 2- bromoethyl-dibromobenzene over a period of 1.2 ks (20 minutes). The mixture was stirred under nitrogen for 11 ks (3 hours) at 7 Hz (420 rpm) at 303 K. (30° C.). The product was diluted with 1-1 of water and the phases were separated. The organic phase was washed with two 1-1 portions of water, dried over calcium sulfate (Drierite), vacuum stripped at 33 Pa (0.2 torr) for 1.8 ks (30 minutes), then treated with 5 g of activated carbon (Nuchar S-A) for 3.6 ks (1 hour) and filtered. 400 ppm of tert-butylcatechol was added as a polymerization inhibitor. The yield of yellow product was 410 g (68.2 percent of theory). GC analysis indicated 0.1 percent ar-bromostyrene, 98.7 percent ar-dibromostyrene, and 1.2 percent ar-tribromostyrene.

Methanol precipitation and gel permeation chromatography both showed less than 0.1 percent polymer in the product.

I claim:

1. A process for the preparation of a bromostyrene, said process comprising heating a haloethyl bromobenzene other than 2-bromoethyl dibromobenzene at a temperature sufficient to dehydrohalogenate and form a bromostyrene, said process being conducted in the presence of an alkaline mixture of
   (i) a promoter quantity of aqueous t-alkoxide ion, and
   (ii) a catalytic quantity of a phase transfer catalyst.

2. The process of claim 1 wherein said haloethyl bromobenzene is a 1-haloethyl bromobenzene, a 2-haloethyl bromobenzene, or a 1-methyl-2-haloethyl bromobenzene and the bromostyrene formed is a bromostyrene or a brominated alpha-methylstyrene.

3. The process of claim 1 wherein said temperature is from about 0° to about 150° C.

4. The process of claim 1 wherein said temperature is from about 20° C. to about 45° C.

5. The process of claim 1 wherein said phase transfer catalyst is a quaternary ammonium salt.

6. The process of claim 1 wherein said phase transfer catalyst is triethylamyl ammonium bromide.

7. The process of claim 1 wherein said alkoxide ion is t-butoxide.

8. A process for the preparation of a bromostyrene, said process comprising heating 250–450 parts by weight haloethyl bromobenzene other than 2-bromoethyl dibromostyrene at about 20°–70° C.; said process being conducted in the presence of a mixture of
   (i) about 100 to about 300 parts 50 percent by weight of sodium hydroxide solution, substantially saturated with sodium chloride,
   (ii) about 3 to about 10 parts by weight of 2-methyl-2-hydroxy-propane, and
   (iii) about 1 part to about 6 parts by weight of triethylpentyl ammonium bromide.

9. The process of claim 7 wherein said haloethyl bromobenzene is a 1-haloethyl mono- or poly-bromobenzene, a 2-haloethyl mono- or poly-bromobenzene, or a 1-methyl-2-haloethyl brominated benzene.

10. The process of claim 9 wherein said haloethyl bromobenzene is a bromoethyl polybromostyrene.

11. A process for the preparation of a bromostyrene, said process comprising (A) heating a reaction mixture comprising (i) a haloethyl bromobenzene other than 2-bromoethyl dibromobenzene, (ii) an aqueous alkali metal hydroxide solution containing a tert-alkoxide promoter, (iii) a lower ter-alcohol and (iv) a phase transfer catalyst and (B) recovering an ar-bromostyrene.

12. A process of claim 11 wherein said alkali metal hydroxide is sodium hydroxide or potassium hydroxide.

13. A process of claim 11 wherein said alkali metal hydroxide solution is a substantially saturated aqueous sodium hydroxide solution.

14. A process of claim 11 wherein said tert-alcohol is ter-butanol and said tert-alkoxide promoter is tert-butoxide.

15. A process of claim 14 wherein said alkali metal hydroxide solution is a substantially saturated aqueous sodium hydroxide solution.

16. A process of claim 15 wherein said phase transfer catalyst is a tetraalkyl quaternary ammonium halide containing about 8–17 carbon atoms.

17. A process of claim 16 wherein said phase transfer catalyst is triethylpentyl ammonium bromide.

18. An aqueous alkaline dehydrohalogenation solution, said solution comprising water, an alkali metal hydroxide, a tert-alcohol, tert-alkoxide anions and a phase transfer catalyst.

19. An aqueous alkaline dehydrohalogenation solution of claim 18 wherein said alkali metal hyroxide is sodium hydroxide, said tert-alcohol is tert-butanol, said tert-alkoxide anion is tert-butoxide and said phase transfer catalyst is a tetraalkyl quaternary ammonium halide.

* * * * *

UNITED STATES PATENT AND TRADEMARK OFFICE
CERTIFICATE OF CORRECTION

PATENT NO. : 4,686,311

DATED : AUGUST 11, 1987

INVENTOR(S) : PHILIP F. JACKISCH

It is certified that error appears in the above-identified patent and that said Letters Patent is hereby corrected as shown below:

Column 1, line 38, reads "CaCl2" and should read --$CaCl_2$--.

Column 2, line 51, reads "benzene 2-haloethyl" and should read -- benzene, 2-haloethyl --.

Column 6, line 42, reads "ter-alcohol" and should read -- tert-alcohol --.

Column 6, line 50, reads "ter-butanol" and should read -- tert-butanol --.

Signed and Sealed this

Sixteenth Day of February, 1988

Attest:

DONALD J. QUIGG

*Attesting Officer*

*Commissioner of Patents and Trademarks*